United States Patent
Ying et al.

(10) Patent No.: US 10,144,925 B2
(45) Date of Patent: Dec. 4, 2018

(54) PREPARATION METHOD OF YEAST CELL IMMOBILIZATION MEDIUM AND APPLICATION THEREOF

(71) Applicant: NANJING UNIVERSITY OF TECHNOLOGY, Nanjing, Jiangsu (CN)

(72) Inventors: Hanjie Ying, Nanjing (CN); Yong Chen, Nanjing (CN); Qingguo Liu, Nanjing (CN); Jinglan Wu, Nanjing (CN); Xiaochun Chen, Nanjing (CN); Jingjing Xie, Nanjing (CN)

(73) Assignee: Nanjing University of Technology, Jiangsu (CN)

( * ) Notice: Subject to any disclaimer, the term of this patent is extended or adjusted under 35 U.S.C. 154(b) by 471 days.

(21) Appl. No.: 14/651,071

(22) PCT Filed: Dec. 13, 2012

(86) PCT No.: PCT/CN2012/086600
§ 371 (c)(1),
(2) Date: Sep. 18, 2015

(87) PCT Pub. No.: WO2014/089811
PCT Pub. Date: Jun. 19, 2014

(65) Prior Publication Data
US 2016/0032272 A1   Feb. 4, 2016

(51) Int. Cl.
| | | |
|---|---|---|
| *C12N 11/08* | (2006.01) |
| *C12N 11/12* | (2006.01) |
| *C12P 7/06* | (2006.01) |
| *C12N 11/02* | (2006.01) |
| *D06M 13/123* | (2006.01) |
| *D06M 13/332* | (2006.01) |
| *D06M 13/418* | (2006.01) |
| *D06M 15/59* | (2006.01) |

(52) U.S. Cl.
CPC ............ *C12N 11/08* (2013.01); *C12N 11/02* (2013.01); *C12N 11/12* (2013.01); *C12P 7/06* (2013.01); *D06M 13/123* (2013.01); *D06M 13/332* (2013.01); *D06M 13/418* (2013.01); *D06M 15/59* (2013.01); *Y02E 50/17* (2013.01)

(58) Field of Classification Search
CPC ......... C12N 11/08; C12N 11/02; C12N 11/12; D06M 13/123; D06M 13/332; D06M 13/418; D06M 15/59; Y02E 50/17
USPC ......................................................... 435/161
See application file for complete search history.

(56) References Cited

U.S. PATENT DOCUMENTS

| | | | | |
|---|---|---|---|---|
| 5,580,644 A | * | 12/1996 | Minami | ................ D04H 13/00 156/253 |
| 2013/0244942 A1 | * | 9/2013 | Benedict | ............... A61L 27/427 514/16.7 |

OTHER PUBLICATIONS

Vieira et al., Could the Improvement in the Alcoholic Fermentation of High Glucose Concentrations by Yeast Immobilization be Explained by Media Supplementation?, Biotechnology Letter, vol. 11, No. 2 (1989) pp. 137-140.*
Kilonzo et al., Effects of surface treatment and process parameters on immobilization of recombinant yeast cells by adoption to fibrous matrices, Bioresource Technology, 102, available online Nov. 19, 2010, pp. 3662-3672.*
Miles et al., The increase in Denaturation Temperature Following Cross-linking of Collagen is Caused by Dehydration of the Fibres, Journal of Molecular Biology, 346 (2005), pp. 551-556.*

* cited by examiner

*Primary Examiner* — Jennifer M. H. Tichy
(74) *Attorney, Agent, or Firm* — Lewis Roca Rothgerber Christie LLP

(57) ABSTRACT

Provided is a preparation method of a yeast cell immobilization medium, which comprises the following steps: (1) boiling a fiber material in boiling water and drying the fiber material; (2) soaking the fiber material in a surface modified aqueous solution with a concentration of 1-100 g/L, using hydrochloric acid to adjust a PH of the solution to 7.0, fully rinsing the fiber material in deionized water and drying the fiber material; (3) soaking the fiber material in a cross-linking agent aqueous solution with a concentration of 1-100 g/L, fully rinsing the fiber material in deionized water and drying the fiber material; and (4) attaching the fiber material to supporting framework. Also provided is the yeast cell immobilization medium prepared using the preparation method and a method for producing ethanol using the yeast cell immobilization medium.

17 Claims, 1 Drawing Sheet

PREPARATION METHOD OF YEAST CELL IMMOBILIZATION MEDIUM AND APPLICATION THEREOF

CROSS-REFERENCE TO RELATED APPLICATION(S)

This application is a National Phase Patent Application and claims priority to and the benefit of International Application Number PCT/CN2012/086600, filed on Dec. 13, 2012, the entire content of which is incorporated herein by reference.

TECHNICAL FIELD

The present invention belongs to the field of industrial biotechnology, relates to a preparation method of a yeast cell immobilization medium and application thereof, and specifically relates to a preparation method of a yeast cell immobilization medium and a method of producing ethanol by using the yeast cell immobilization medium.

BACKGROUND

As a renewable clean energy, ethanol has become a research focus in the field of industrial biotechnology. Free cells are used in traditional ethanol fermentation technology, in which the yeasts flow away with the fermenting mash, resulting in in-sufficient yeast concentration in the fermentation tank, slow ethanol fermentation and long fermentation time.

In recent years, immobilized yeast has obtained more and more attention and application in the fermentation production of fuel ethanol. The nature of the immobilized cell technology is to use physical or chemical means to localize free cells in defined space region but make them keep catalytic activity and reused repeatedly so as to reduce cell loss due . With the development of the immobilization technology, studies on immobilization method and carrier material become more and more extensive. It is found that immobilized yeast fermentation can affect physiological properties and metabolic activity of yeast cells, such as cell morphology, intracellular osmotic pressure and membrane permeability and so forth. Meanwhile, immobilized yeast can also improve the tolerance of yeast cells to fermentation inhibitors and fermentation environment.

Due to gathering of massive yeast cells on carriers after immobilization, certain concentration advantage is obtained which protects the yeasts from being contaminated by other microbes.

There are more and more immobilization methods applied to yeast cells at present and common immobilization methods include embedding method and adsorption method.

The embedding method is the most common and the most extensively studied immobilization method, which is a method to immobilize microbial cells by intercepting the cells in the pores of a gridding made of water-insoluble polymer compounds. The embedding method generally includes the embedding method using natural carriers and the embedding method using synthetic organic polymer carriers. The natural embedding carriers include agar, caragneenan, calcium alginate, sodium alginate and polyvinyl alcohol and the like. They have advantages in non-toxicity to organisms, easy molding and high immobilization density, but they have low mechanical strength, weak mass transfer and poor resistance to microbial decomposition; while the synthetic organic polymer carriers such as polyacrylamide, polyvinyl alcohol and polyacrylic acid have high mechanical strength and stable chemical properties, but forming a polymer network during immobilization requires harsh conditions which would cause great harm to cells; on the other hand, since cells are inside the network materials, there are some problems of weak mass transfer, thalli death at the later stage and low catalytic efficiency.

The adsorption method utilizes the adsorbability of microorganism to a solid surface or the surface of other cells to make it adsorbed to the surface of water-insoluble carriers and thereby immobilized. The adsorption method includes physical adsorption and ion adsorption. The physical adsorption immobilizes a microorganism by using the materials with strong adsorbability, such as silica gel and active carbon; while the ion adsorption makes microbial cells adsorbed to ion-exchanger by electrostatic interaction. The advantages of the adsorption method lie in easy operation, utilizing ion-exchanger which is stable and not easy to be decomposed, and less effect on cell activity, but the shortage is that the adsorbent material in the method cannot be used repeatedly very well.

SUMMARY OF THE INVENTION

Against the deficiencies of the prior art, the present invention provides a novel yeast cell surface immobilization medium which immobilizes the yeast cell by a fiber material, which overcomes the deficiencies of the prior art. The immobilization method has not only stable process, no toxicity and good adsorption but also excellent effects on protecting and promoting cell activity and cell growth. Using the yeast cells immobilized by the medium to produce ethanol by fermentation can ensure a stable fermentation and highly effective constant production but also reduce energy consumption during ethanol separation.

To achieve the above objectives, the present invention adopts the following technical solutions:

A preparation method of a yeast cell immobilization medium, which comprises the following steps:
(1) Boiling a fiber material in boiling water followed by drying;
(2) Soaking the fiber material in a surface modifier aqueous solution at a concentration of 1-100 g/L, adjusting the pH of the solution to 7.0 with hydrochloric acid, and then fully rinsing the fiber material in deionized water
(3) Soaking the fiber material in a cross-linking agent aqueous solution at a concentration of 1-100 g/L, and then fully rinsing the fiber material in deionized water followed by drying;
(4) Attaching the fiber material to a supporting framework.

In the above preparation method, preferably, said surface modifier is one or more selected from a group consisting of polyetherimide, diethylenetriamine, dimethylaminopropylamine, polyethyleneimine and succinimide;

In the above preparation method, preferably, said fiber material is one or more selected from a group consisting of cotton fabric; activated carbon fabric; polyester fiber; silk; bamboo fiber; polyvinyl alcohol fiber such as vinylon; non-woven fabrics such as dacron, polypropylene fiber, nylon, spandex and acrylic; polyurethane foam; bagasse and cornstalk.

In the above preparation method, preferably, the concentration of said hydrochloric acid is 0.5-2 mol/L.

In the above preparation method, preferably, said cross-linking agent is one or more selected from a group consisting of glutaraldehyde, glyoxal, succinaldehyde, 2-methyl-1,3-malondialdehyde and (2S,3R)-2,3-dihydroxyl succinaldehyde.

In the above preparation method, preferably, said supporting framework is steel wire gauze.

As for one specific embodiment of the above preparation method, the method comprises the following steps:
(1) Boiling a fiber material in boiling water for 0.1-10 hours followed by drying at 20-100° C., and storing it at 4° C. for use;
(2) Soaking the fiber material in a surface modifier aqueous solution at a concentration of 1-100 g/L for 1-50 hours, adjusting the pH of the solution to 7.0 with hydrochloric acid, fully rinsing the fiber material in deionized water followed by drying at 60° C., and storing it at 4° C. for use;
(3) Soaking the fiber material in a cross-linking agent aqueous solution at a concentration of 1-100 g/L for 1-50 hours, fully rinsing the fiber material in deionized water followed by drying at 60° C., and storing it at 4° C. for use;
wherein, said surface modifier is one or more selected from a group consisting of polyetherimide, diethylenetriamine, dimethylaminopropylamine, polyethyleneimine and succinimide;
(4) Tiling the fiber material on a supporting framework to make it attached to the supporting framework, and then rolling it into a cylinder.

The present invention also provides a yeast cell immobilization medium prepared according to the above preparation method.

In another aspect, the present invention provides a method of producing ethanol via fermentation by using said yeast cell immobilization medium, comprising the following steps:
(1) Firstly, cultivating yeast cells in a seed growth medium till logarithmic growth phase to obtain a seed broth, then circulating the seed broth through said yeast cell immobilization medium in a bioreactor to immobilize the yeast cells onto the medium; wherein, said seed broth comprises 10-100 g/L of glucose, 10-100 g/L of peptone, 10-100 g/L of yeast extract, 0.2-10 g/L of anhydrous magnesium sulfate, 0.1-10 g/L of ammonium sulfate and 0.5-15 g/L of phosphate, with a pH of 4-6.
(2) Discharging the solution in the bioreactor when the OD value of the solution is decreased slowly or lower than 1, adding fermentation medium into the bioreactor, allowing for circulation fermentation; wherein, said fermentation medium comprises 100-400 g/L of glucose, 0.5-20 g/L of peptone, 0.5-20 g/L of yeast extract, 0.1-10 g/L of ammonium sulfate, 0.5-10 g/L of phosphate, 0.05-1 g/L of ferrous sulfate heptahydrate and 0.05-1 g/L of zinc sulfate heptahydrate, with a pH of 4-6.5; or said fermentation medium is cassava hydrolysate or plant stalk hydrolysate comprising 0.1-10 g/L of urea and 0.1-10 g/L of magnesium sulfate.

As for one specific embodiment of the above method, the method comprises the following steps:
(1) Firstly, cultivating yeast cells in a seed growth medium till logarithmic growth phase to obtain a seed broth, then circulating the seed broth through said yeast cell immobilization medium in a bioreactor at 30-42° C. to immobilize the yeast cells onto the medium; wherein, said seed broth has a flow velocity of 0.5-50 L/h, and said seed growth medium comprises 10-100 g/L of glucose, 10-100 g/L of peptone, 10-100 g/L of yeast extract, 0.2-10 g/L of anhydrous magnesium sulfate, 0.1-10 g/L of ammonium sulfate and 0.5-15 g/L of phosphate, with a pH of 4-6; the filling content of the fiber material in said bioreactor is 5-150 g/L;
(2) Discharging the solution in the bioreactor when the OD value of the solution is decreased slowly or lower than 1, adding fermentation medium into the bioreactor, allowing for circulation fermentation at 30-42° C.; wherein, said fermentation medium comprises 100-400 g/L of glucose, 0.5-20 g/L of peptone, 0.5-20 g/L of yeast extract, 0.1-10 g/L of ammonium sulfate, 0.5-10 g/L of phosphate, 0.05-1 g/L of ferrous sulfate heptahydrate and 0.05-1 g/L of zinc sulfate heptahydrate, with a pH of 4-6.5; or said fermentation medium is cassava hydrolysate or plant stalk hydrolysate comprising 0.1-10 g/L of urea and 0.1-10 g/L of magnesium sulfate; the circulating velocity of the fermentation broth is 0.5-50 L/h.

Compared to the prior art, the present invention obtains the following beneficial effects:
1. The immobilization material prepared according to the present invention is low-cost, non-toxic and has high mechanical strength; the material is chemically inert and thereby is non-toxic to cells and not be degraded by cells; it will not affect the growth and metabolism of microorganisms, dead cells are detached automatically and living cells can achieve self-proliferation, so that high catalytic efficiency can be maintained all the time.
2. Since the fiber material has a high porosity (>95%) and a high specific surface area (>40 $m^2/m^3$), it can immobilize cells in a high density (maximum cell density up to 70 g/L) but also results in good mass transfer performance, i.e. the mass transfer efficiency is high and the fermentation time is shortened by more than a half, for example, the ethanol fermentation time with glucose as a substrate is decreased from 20 hours to 6-8 hours, the ethanol fermentation time (saccharification, liquefaction and fermentation as a whole) with cassava, corn, molasses and other starchy food crops as a substrate is also decreased from 30-50 hours to 8-15 hours, and the ethanol fermentation time with the hydrolysate of cornstalk, wheat stalk or corncob as a substrate is decreased from 30-40 hours to 10-15 hours as well.
3. The immobilization medium of the present invention can also improve the tolerance of the yeast strain to ethanol, under the same conversion rate, the concentration of the product is increased from 90-110 g/L to 120-150 g/L, and the density of thalli in the effluent is very low, which makes the separation cost at a later stage reduced significantly.

BRIEF DESCRIPTION OF THE DRAWINGS

Hereinafter, the embodiments of the invention will be described in details with reference to the accompanying drawings, wherein.

BEST MODES

The present invention will be further described hereinafter in combination with specific examples. Those skilled in the art shall appreciate that the examples set forth are only for illustrating the present invention but not intended to limit the scope of the invention.

Unless otherwise specified, the experiment methods in the following examples are all conventional methods; the raw materials and reagents used in the following examples are all commercially available products.

EXAMPLE 1

Preparation of Ethanol from Glucose by Using Surface Immobilization Medium Prepared From Active Carbon Fiber Cotton Firstly, the active carbon fiber cotton was stewed in boiling water for 1 hour, followed by drying in a drying oven at 80° C.; then the dried fiber material was soaked in a 10 g/L succibimide solution for 2 hours and rinsed with distilled water; then the preliminarily processed fiber material was soaked in a 10 g/L cross-linking agent 2-methyl-1,3-malondialdehyde aqueous solution, allowing for reaction for 2 hours followed by rinsing with distilled water; finally the fiber material was dried in a drying oven at 60-80° C.

Figure 1:
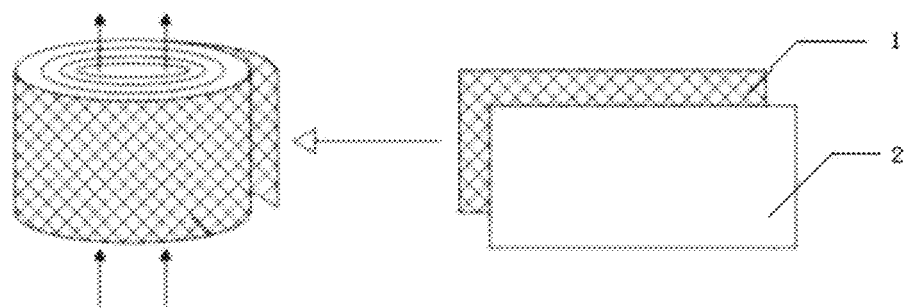
FIG. 1 is an operation diagram for attaching a fiber material to a supporting framework.
Figure 2:
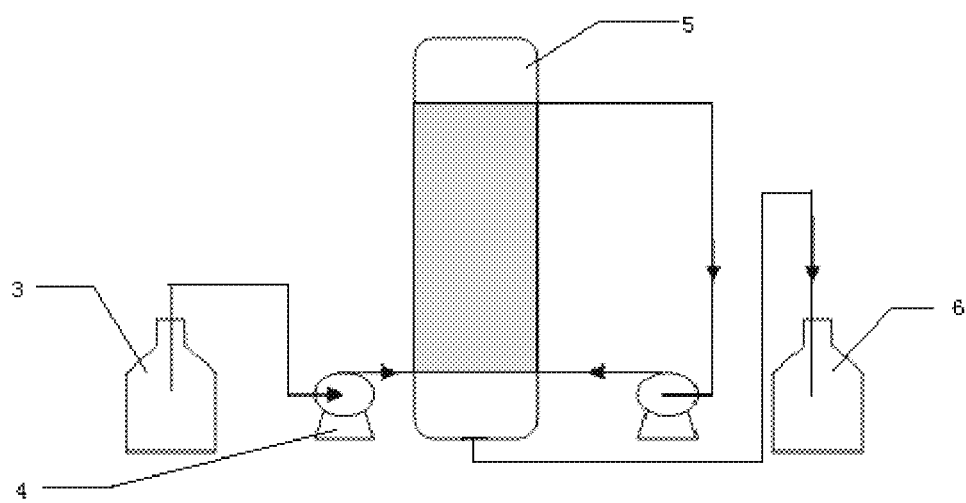
FIG. 2 is a schematic diagram for the method of producing ethanol via fermentation by using the yeast cell immobilization medium of the present invention;
wherein, 1 refers to steel wire gauze; 2 refers to fiber material; 3 refers to feeding tank; 4 refers to pump; 5 refers to bioreactor and 6 refers to product collecting tank.

According to FIG. 1, the processed fiber material 1 and the steel wire gauze 2 were cut into the same size and shape, then the fiber material was tiled on the steel wire gauze, rolled into a cylinder together with the steel wire gauze, where it should be maintained loose and uniform between each layers of the fiber material, and then the cylinder was loaded into the reactor 5 with a height-diameter ratio of 4.

Then the cultivated strains were charged into the feeding tank 3: the seed broth was flowed rapidly into the reactor 5 from the bottom by the pump 4, the pump 4 was shut off when the reactor 5 was filled up with the seed broth, the circulating pump 4 on the right side was switched on, allowing for circulation immobilization for 36 hours at a flow velocity of 2 L/h, until the thalli concentration in the feeding tank 3 became very low without significant decrease. The effluent was discharged from the bottom of the reactor 5. The fermentation medium (with a glucose concentration of 250 g/L) was added rapidly through the feeding tank 3; after the reactor 5 was filled up, the feeding pump 4 was shut off accordingly, allowing for circulation fermentation, wherein, the temperature was 35° C., the pH of the fermentation broth was 4 and the flow velocity was 10 L/h. The fermentation time was 8 hours and the product concentration was 120 g/L, 14 hours shorter than free fermentation. The fermentation was conducted for 20 batches, then the average fermentation time was reduced to 7 hours, and the productivity of ethanol reached 17.1 $gL^{-1}h^{-1}$ and the average yield was 48%.

EXAMPLE 2

Preparation of Ethanol from Cassava by Using Surface Immobilization Medium Prepared From Cotton Fabric Firstly, the cotton fabric was stewed in boiling water for 1 hour, followed by drying in a drying oven at 80° C.; then the dried fiber material was soaked in a 15 g/L polyethyleneimine solution for 4 hours and rinsed with distilled water; then the preliminarily processed fiber material was soaked in a 20 g/L cross-linking agent glyoxal aqueous solution, allowing for reaction for 4 hours followed by rinsing with distilled water; finally the fiber material was dried in a drying oven at 60-80° C.

During fermentation, the cassava feed liquid was subjected to enzymatic hydrolysis at the same time of fermentation (the glucose concentration in the cassava feed liquid after saccharification was about 245 g/L) according to the device and method described in Example 1, wherein, the temperature was 34° C., the pH of the fermentation broth was 4.5 and the flow velocity was 20 L/h. 18 hours after fermentation of the first batch, the glucose was almost depleted and the concentration of ethanol was up to 110 g/L. When fermentation of 15 batches were completed, the average fermentation time was 20 hours, and the average productivity of ethanol was 7 $gL^{-1}h^{-1}$ and the average yield was 47%.

EXAMPLE 3

Preparation of Ethanol from Fiber by Using Surface Immobilization Medium Prepared from Dacron Firstly, the dacron was stewed in boiling water for 1 hour, followed by drying in a drying oven at 80° C.; then the dried dacron was soaked in a 5 g/L polyethyleneimine solution for 3 hours and rinsed with distilled water; then the preliminarily processed dacron was soaked in a 15 g/L cross-linking agent glutaraldehyde aqueous solution, allowing for reaction for 2 hours followed by rinsing with distilled water; finally the decron was dried in a drying oven at 60-80° C.

During fermentation, the stalk hydrolysate (the glucose concentration in the hydrolysate was about 110 g/L) was subjected to fermentation according to the device and method described in Example 1, wherein, the temperature was 34° C., the pH of the fermentation broth was 4.5 and the flow velocity was 27 L/h. 14 hours after fermentation of the first batch, the glucose was almost depleted and the concentration of ethanol was up to 52.85 g/L. When fermentation of 10 batches was completed, the average fermentation time was 15 hours, and the average productivity of ethanol was 3.6 $gL^{-1}h^{-1}$ and the average conversion rate was 47.3%.

The invention claimed is:

1. A preparation method of a yeast cell immobilization medium, which comprises the following steps:
   (1) boiling a fiber material in a medium consisting of boiling water followed by drying;
   (2) soaking the fiber material in a surface modifier aqueous solution at a concentration of 1-100 g/L, adjusting a pH of the solution to 7.0 with hydrochloric acid, and then fully rinsing the fiber material in deionized water followed by drying;
   (3) soaking the fiber material in a cross-linking agent aqueous solution at a concentration of 1-100 g/L, and then fully rinsing the fiber material in deionized water followed by drying; and
   (4) attaching the fiber material to a supporting framework, wherein, said surface modifier is succinimide, and said cross-linking agent is 2-methyl-1,3-malondialdehyde.

2. The preparation method according to claim 1, wherein said fiber material is one or more selected from the group consisting of cotton fabric; activated carbon fabric; polyester fiber; silk; bamboo fiber; polyvinyl alcohol fiber; non-woven fabrics; polyurethane foam; bagasse and cornstalk.

3. The preparation method according to claim 2, wherein said polyvinyl alcohol fiber is vinylon.

4. The preparation method according to claim 2, wherein said non-woven fabrics is selected from a group consisting of dacron, polypropylene fiber, nylon, spandex and acrylic.

5. The preparation method according to claim 2, wherein said activated carbon fabric is activated carbon fabric cotton.

6. The preparation method according to claim 1, wherein a concentration of said hydrochloric acid is 0.5-2 mol/L.

7. The preparation method according to claim 1, wherein said supporting framework is steel wire gauze.

8. The preparation method according to claim 1, wherein a concentration of succinimide is 10 g/L, and a concentration of 2-methyl-1,-3 -malondialdehyde is 10 g/L.

9. A preparation method of a yeast cell immobilization medium, which comprises the following steps:
   (1) boiling a fiber material in a medium consisting of boiling water for 0.1-10 hours followed by drying at 20-100° C., and storing it at 4° for use;
   (2) soaking the fiber material in a surface modifier aqueous solution at a concentration of 1-100 g/L for 1-50 hours, adjusting a pH of the solution to 7.0 with hydrochloric acid, fully rinsing the fiber material in deionized water followed by drying at 60° C., and storing it at 4° C. for use;
   (3) soaking the fiber material in a cross-linking agent aqueous solution at a concentration of 1-100 g/L for 1-50 hours, fully rinsing the fiber material in deionized water followed by drying at 60° C., and storing it at 4° C. for use; and
   (4) tilinq the fiber material on a supporting framework to make it attached to the supporting framework, and then rolling the framework into a cylinder, wherein, said surface modifier is succinimide, and said cross-linking agent is 2-methyl-1,3-malondialdehyde.

10. The preparation method according to claim 9, wherein said fiber material is one or more selected from the group consisting of cotton fabric; activated carbon fabric; polyester fiber; silk; bamboo fiber; polyvinyl alcohol fiber; non-woven fabrics; polyurethane foam; bagasse and cornstalk.

11. The preparation method according to claim 10, wherein said polyvinyl alcohol fiber is vinylon.

12. The preparation method according to claim 10, wherein said non-woven fabrics is selected from the group consisting of dacron, polypropylene fiber, nylon, spandex and acrylic.

13. The preparation method according to claim 10, wherein said activated carbon fabric is activated carbon fabric cotton.

14. The preparation method according to claim 9, wherein a concentration of said hydrochloric acid is 0.5-2 mol/L.

15. The preparation method according to claim 9, wherein said supporting framework is steel wire gauze.

16. The preparation method according to claim 9, wherein a concentration of succinimide is 10 g/L, and a concentration of 2-methyl-1,3-malondialdehyde is 10 g/L.

17. The preparation method according to claim 9, wherein boiling is 1 hour in step (1), soaking is 2 hours in step (2), and soaking is 2 hours in step (3).

* * * * *